US011090183B2

(12) United States Patent
Sanchez et al.

(10) Patent No.: US 11,090,183 B2
(45) Date of Patent: Aug. 17, 2021

(54) CONTAINER FOR COLLECTING LIQUID FOR TRANSPORT

(71) Applicant: PureWick Corporation, El Cajon, CA (US)

(72) Inventors: Robert A Sanchez, Fallbrook, CA (US); Raymond John Newton, Bonsall, CA (US)

(73) Assignee: PUREWICK CORPORATION, El Cajon, CA (US)

( * ) Notice: Subject to any disclaimer, the term of this patent is extended or adjusted under 35 U.S.C. 154(b) by 0 days.

(21) Appl. No.: 14/952,591

(22) Filed: Nov. 25, 2015

(65) Prior Publication Data

US 2017/0143534 A1    May 25, 2017
US 2017/0252202 A9    Sep. 7, 2017

Related U.S. Application Data

(60) Provisional application No. 62/084,078, filed on Nov. 25, 2014.

(51) Int. Cl.
*A61F 5/44* (2006.01)
*A61M 1/00* (2006.01)

(52) U.S. Cl.
CPC ......... *A61F 5/4404* (2013.01); *A61M 1/0001* (2013.01); *A61M 1/69* (2021.05); *A61M 2210/1092* (2013.01)

(58) Field of Classification Search
CPC .............. A61M 1/0019; A61M 1/0001; A61M 2210/1092; A61F 5/4404

(Continued)

(56) References Cited

U.S. PATENT DOCUMENTS 2,613,670 A    10/1952   Edward
2,644,234 A    7/1953    Earl
(Continued)

FOREIGN PATENT DOCUMENTS

CN    2269203 Y    12/1997
CN    1533755 A    10/2004
(Continued)

OTHER PUBLICATIONS

International Search Report and Written Opinion for International Application No. PCT/US16/49274, dated Dec. 1, 2016, 12 pages.

(Continued)

*Primary Examiner* — Andrew J Mensh
(74) *Attorney, Agent, or Firm* — Dorsey & Whitney LLP

(57) ABSTRACT

A container for collecting liquid for transport, comprising: a web of flexible porous material defining at least a portion of a chamber in which liquid can be collected for transport. The chamber is configured to receive a tube in a position within the chamber that enables the tube to transport liquid from the chamber while the liquid collects within the chamber upon being drawn through the web when a partial vacuum is applied within the chamber via the tube. The porous material comprises a web of spun plastic fibers, such as spun polyester fibers. In one embodiment, the web of spun plastic fibers is configured to define an elongated portion of the chamber. In another embodiment, a backing of non-permeable material covers a portion of the web and is so combined with the web as to further define the chamber.

18 Claims, 2 Drawing Sheets

(58) Field of Classification Search
USPC .......................................................... 604/319
See application file for complete search history.

(56) References Cited

U.S. PATENT DOCUMENTS

| | | | |
|---|---|---|---|
| 2,968,046 A | 1/1961 | Duke | |
| 3,087,938 A | 4/1963 | Hans et al. | |
| 3,198,994 A | 8/1965 | Hildebrandt et al. | |
| 3,312,981 A | 4/1967 | Mcguire et al. | |
| 3,349,768 A | 10/1967 | Keane | |
| 3,366,116 A | 1/1968 | Huck | |
| 3,400,717 A | 9/1968 | Bruce et al. | |
| 3,406,688 A | 10/1968 | Bruce | |
| 3,511,241 A | 5/1970 | Lee | |
| 3,512,185 A | 5/1970 | Ellis | |
| 3,520,300 A * | 7/1970 | Guiles, Jr. | A61M 1/008 604/269 |
| 3,613,123 A | 10/1971 | Langstrom | |
| 3,651,810 A | 3/1972 | Ormerod | |
| 3,726,277 A | 4/1973 | Hirschman | |
| 4,020,843 A | 5/1977 | Kanall | |
| 4,022,213 A | 5/1977 | Stein | |
| 4,200,102 A | 4/1980 | Duhamel et al. | |
| 4,202,058 A | 5/1980 | Anderson | |
| 4,233,025 A | 11/1980 | Larson et al. | |
| 4,246,901 A | 1/1981 | Frosch et al. | |
| 4,257,418 A | 3/1981 | Hessner | |
| 4,270,539 A | 6/1981 | Frosch et al. | |
| 4,352,356 A | 10/1982 | Tong | |
| 4,360,933 A | 11/1982 | Kimura et al. | |
| 4,365,363 A | 12/1982 | Windauer | |
| 4,387,726 A | 6/1983 | Denard | |
| 4,425,130 A | 1/1984 | Desmarais | |
| 4,453,938 A | 6/1984 | Brendling | |
| 4,457,314 A | 7/1984 | Knowles | |
| 4,526,688 A | 7/1985 | Schmidt, Jr. et al. | |
| 4,528,703 A | 7/1985 | Kraus | |
| 4,581,026 A | 4/1986 | Schneider | |
| 4,610,675 A | 9/1986 | Triunfol | |
| 4,627,846 A | 12/1986 | Ternstroem | |
| 4,631,061 A | 12/1986 | Martin | |
| 4,650,477 A | 3/1987 | Johnson | |
| 4,692,160 A | 9/1987 | Nussbaumer | |
| 4,713,066 A | 12/1987 | Komis | |
| 4,747,166 A * | 5/1988 | Kuntz | A61F 5/455 4/144.1 |
| 4,752,944 A | 6/1988 | Conrads et al. | |
| 4,769,215 A | 9/1988 | Ehrenkranz | |
| 4,772,280 A | 9/1988 | Rooyakkers | |
| 4,790,835 A | 12/1988 | Elias | |
| 4,791,686 A | 12/1988 | Taniguchi et al. | |
| 4,795,449 A | 1/1989 | Schneider et al. | |
| 4,799,928 A | 1/1989 | Crowley | |
| 4,804,377 A | 2/1989 | Hanifl et al. | |
| 4,820,297 A | 4/1989 | Kaufman et al. | |
| 4,846,909 A | 7/1989 | Klug et al. | |
| 4,882,794 A | 11/1989 | Stewart, III | |
| 4,883,465 A | 11/1989 | Brennan | |
| 4,886,508 A | 12/1989 | Washington | |
| 4,886,509 A | 12/1989 | Mattsson | |
| 4,889,533 A | 12/1989 | Beecher | |
| 4,905,692 A | 3/1990 | More | |
| 4,955,922 A | 9/1990 | Terauchi | |
| 4,965,460 A | 10/1990 | Tanaka et al. | |
| 5,002,541 A | 3/1991 | Conkling et al. | |
| 5,004,463 A | 4/1991 | Nigay | |
| 5,031,248 A | 7/1991 | Kemper | |
| 5,049,144 A | 9/1991 | Payton | |
| 5,071,347 A | 12/1991 | Mcguire | |
| 5,084,037 A | 1/1992 | Barnett | |
| 5,100,396 A | 3/1992 | Zamierowski | |
| 5,147,301 A | 9/1992 | Ruvio | |
| 5,195,997 A | 3/1993 | Carns | |
| 5,203,699 A | 4/1993 | Mcguire | |
| 5,244,458 A | 9/1993 | Takasu | |
| 5,294,983 A | 3/1994 | Ersoz et al. | |
| 5,295,983 A | 3/1994 | Kubo | |
| 5,300,052 A | 4/1994 | Kubo | |
| 5,382,244 A | 1/1995 | Telang | |
| 5,466,229 A | 11/1995 | Elson et al. | |
| 5,478,334 A | 12/1995 | Bernstein | |
| 5,499,977 A | 3/1996 | Marx | |
| D373,928 S | 9/1996 | Green | |
| 5,618,277 A | 4/1997 | Goulter | |
| 5,628,735 A | 5/1997 | Skow | |
| 5,636,643 A | 6/1997 | Argenta et al. | |
| 5,674,212 A | 10/1997 | Osborn, III et al. | |
| 5,678,564 A | 10/1997 | Lawrence et al. | |
| 5,678,654 A | 10/1997 | Uzawa | |
| 5,687,429 A | 11/1997 | Rahlff | |
| 5,695,485 A | 12/1997 | Duperret et al. | |
| 5,752,944 A | 5/1998 | Dann et al. | |
| 5,772,644 A | 6/1998 | Bark et al. | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,865,378 A | 2/1999 | Hollinshead et al. | |
| 5,887,291 A | 3/1999 | Bellizzi | |
| 5,894,608 A | 4/1999 | Birbara | |
| D409,303 S | 5/1999 | Oepping | |
| 5,911,222 A | 6/1999 | Lawrence et al. | |
| 5,957,904 A | 9/1999 | Holland | |
| 5,972,505 A | 10/1999 | Phillips et al. | |
| 6,059,762 A | 5/2000 | Boyer et al. | |
| 6,063,064 A | 5/2000 | Tuckey et al. | |
| 6,105,174 A | 8/2000 | Karlsten et al. | |
| 6,113,582 A | 9/2000 | Dwork | |
| 6,117,163 A | 9/2000 | Bierman | |
| 6,123,398 A | 9/2000 | Arai et al. | |
| 6,129,718 A | 10/2000 | Wada et al. | |
| 6,131,964 A | 10/2000 | Sareshwala | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,248,096 B1 | 6/2001 | Dwork et al. | |
| 6,311,339 B1 | 11/2001 | Kraus | |
| 6,336,919 B1 | 1/2002 | Davis et al. | |
| 6,338,729 B1 | 1/2002 | Wada et al. | |
| 6,409,712 B1 | 6/2002 | Dutari et al. | |
| 6,416,500 B1 | 7/2002 | Wada et al. | |
| 6,475,198 B1 | 11/2002 | Lipman et al. | |
| 6,479,726 B1 * | 11/2002 | Cole | A61F 13/471 604/317 |
| 6,491,673 B1 | 12/2002 | Palumbo et al. | |
| 6,508,794 B1 | 1/2003 | Palumbo et al. | |
| 6,540,729 B1 | 4/2003 | Wada et al. | |
| 6,547,771 B2 | 4/2003 | Robertson et al. | |
| 6,569,133 B2 | 5/2003 | Cheng et al. | |
| 6,592,560 B2 | 7/2003 | Snyder et al. | |
| 6,620,142 B1 | 9/2003 | Flueckiger | |
| 6,629,651 B1 | 10/2003 | Male et al. | |
| 6,635,038 B2 | 10/2003 | Scovel | |
| 6,685,684 B1 | 2/2004 | Falconer | |
| 6,702,793 B1 | 3/2004 | Sweetser et al. | |
| 6,706,027 B2 | 3/2004 | Harvie et al. | |
| 6,732,384 B2 | 5/2004 | Scott | |
| 6,740,066 B2 | 5/2004 | Wolff et al. | |
| 6,783,519 B2 | 8/2004 | Samuelsson | |
| 6,814,547 B2 | 11/2004 | Childers et al. | |
| 6,849,065 B2 | 2/2005 | Schmidt et al. | |
| 6,857,137 B2 | 2/2005 | Otto | |
| 6,885,690 B2 | 4/2005 | Aggerstam et al. | |
| 6,888,044 B2 | 5/2005 | Fell et al. | |
| 6,912,737 B2 | 7/2005 | Ernest et al. | |
| 6,918,899 B2 | 7/2005 | Harvie | |
| 6,979,324 B2 | 12/2005 | Byebordi et al. | |
| 7,018,366 B2 | 3/2006 | Easter | |
| 7,066,411 B2 | 6/2006 | Male et al. | |
| 7,125,399 B2 | 10/2006 | Miskie | |
| 7,131,964 B2 | 11/2006 | Harvie | |
| 7,135,012 B2 | 11/2006 | Harvie | |
| 7,141,043 B2 | 11/2006 | Harvie | |
| 7,171,699 B2 | 2/2007 | Ernest et al. | |

(56) References Cited

U.S. PATENT DOCUMENTS

| | | |
|---|---|---|
| 7,171,871 B2 | 2/2007 | Kozak |
| 7,179,951 B2 | 2/2007 | Krishnaswamy-mirle et al. |
| 7,181,781 B1 | 2/2007 | Trabold et al. |
| 7,186,245 B1 | 3/2007 | Cheng et al. |
| 7,192,424 B2 | 3/2007 | Cooper |
| 7,220,250 B2 | 5/2007 | Suzuki et al. |
| 7,335,189 B2 | 2/2008 | Harvie |
| 7,358,282 B2 | 4/2008 | Krueger et al. |
| 7,390,320 B2 | 6/2008 | Machida et al. |
| 7,488,310 B2 | 2/2009 | Yang |
| D591,106 S | 4/2009 | Dominique et al. |
| 7,520,872 B2 | 4/2009 | Biggie et al. |
| D593,801 S | 6/2009 | Wilson et al. |
| 7,588,560 B1 | 9/2009 | Dunlop |
| 7,682,347 B2 | 3/2010 | Parks et al. |
| 7,695,459 B2 | 4/2010 | Gilbert et al. |
| 7,695,460 B2 | 4/2010 | Wada et al. |
| 7,699,818 B2 | 4/2010 | Gilbert |
| 7,699,831 B2 | 4/2010 | Bengtson et al. |
| 7,722,584 B2 | 5/2010 | Tanaka et al. |
| 7,727,206 B2 | 6/2010 | Gorres |
| 7,740,620 B2 | 6/2010 | Gilbert et al. |
| 7,749,205 B2 | 7/2010 | Tazoe et al. |
| 7,755,497 B2 | 7/2010 | Wada et al. |
| 7,766,887 B2 | 8/2010 | Burns, Jr. et al. |
| 7,833,169 B2 | 11/2010 | Hannon |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 * | 3/2011 | Mombrinie ............ A47L 7/0042 |
| | | 604/317 |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,947,025 B2 | 5/2011 | Buglino et al. |
| 7,976,519 B2 | 7/2011 | Bubb et al. |
| 7,993,318 B2 | 8/2011 | Olsson et al. |
| 8,028,460 B2 | 10/2011 | Williams |
| 8,128,608 B2 | 3/2012 | Thevenin |
| 8,181,651 B2 | 5/2012 | Pinel |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 * | 10/2012 | Sanchez ............... A61F 5/4404 |
| | | 604/317 |
| 8,303,554 B2 | 11/2012 | Tsai et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| D676,241 S | 2/2013 | Merrill |
| 8,388,588 B2 | 3/2013 | Wada et al. |
| 8,425,482 B2 | 4/2013 | Khoubnazar |
| 8,546,639 B2 | 10/2013 | Wada et al. |
| 8,551,075 B2 | 10/2013 | Bengtson |
| 8,568,376 B2 | 10/2013 | Delattre et al. |
| 8,585,683 B2 | 11/2013 | Bengtson et al. |
| D704,330 S | 5/2014 | Cicatelli |
| D704,510 S | 5/2014 | Mason et al. |
| D705,423 S | 5/2014 | Walsh Cutler |
| 8,715,267 B2 | 5/2014 | Bengtson et al. |
| 8,864,730 B2 | 10/2014 | Conway et al. |
| 8,936,585 B2 | 1/2015 | Carson et al. |
| D729,581 S | 5/2015 | Boroski |
| 9,028,460 B2 | 5/2015 | Medeiros |
| 9,173,602 B2 | 11/2015 | Gilbert |
| 9,173,799 B2 | 11/2015 | Tanimoto et al. |
| 9,248,058 B2 | 2/2016 | Conway et al. |
| 9,480,595 B2 | 11/2016 | Baham et al. |
| D777,941 S | 1/2017 | Piramoon |
| D804,907 S | 12/2017 | Sandoval |
| D814,239 S | 4/2018 | Arora |
| 10,226,376 B2 | 3/2019 | Sanchez et al. |
| 10,335,121 B2 | 7/2019 | Desai |
| 10,376,406 B2 | 8/2019 | Newton |
| 10,390,989 B2 | 8/2019 | Sanchez et al. |
| 10,478,356 B2 | 11/2019 | Griffin |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0189992 A1 | 12/2002 | Schmidt et al. |
| 2003/0004436 A1 | 1/2003 | Schmidt et al. |
| 2003/0120178 A1 | 6/2003 | Heki |
| 2003/0181880 A1 | 9/2003 | Schwartz |
| 2003/0195484 A1 | 10/2003 | Harvie |
| 2003/0233079 A1 | 12/2003 | Parks et al. |
| 2004/0006321 A1 | 1/2004 | Cheng et al. |
| 2004/0056122 A1 | 3/2004 | Male et al. |
| 2004/0127872 A1 * | 7/2004 | Petryk ............... A61F 13/51305 |
| | | 604/382 |
| 2004/0128749 A1 | 7/2004 | Scott |
| 2004/0143229 A1 | 7/2004 | Easter |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0070861 A1 | 3/2005 | Okabe et al. |
| 2005/0070862 A1 | 3/2005 | Tazoe et al. |
| 2005/0097662 A1 | 5/2005 | Leimkuhler et al. |
| 2005/0101924 A1 | 5/2005 | Elson et al. |
| 2005/0177070 A1 | 8/2005 | Levinson et al. |
| 2005/0197639 A1 | 9/2005 | Mombrinie |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 * | 1/2006 | Suzuki .................... A61F 5/451 |
| | | 604/329 |
| 2006/0155214 A1 | 7/2006 | Wightman |
| 2006/0200102 A1 | 9/2006 | Cooper |
| 2006/0229576 A1 | 10/2006 | Conway et al. |
| 2006/0231648 A1 | 10/2006 | Male et al. |
| 2006/0235359 A1 | 10/2006 | Marland |
| 2007/0006368 A1 | 1/2007 | Key et al. |
| 2007/0038194 A1 | 2/2007 | Wada et al. |
| 2007/0117880 A1 | 5/2007 | Elson et al. |
| 2007/0135786 A1 | 6/2007 | Schmidt et al. |
| 2007/0191804 A1 | 8/2007 | Coley |
| 2007/0214553 A1 | 9/2007 | Carromba et al. |
| 2007/0266486 A1 | 11/2007 | Ramirez |
| 2008/0004576 A1 | 1/2008 | Tanaka et al. |
| 2008/0015527 A1 | 1/2008 | House |
| 2008/0033386 A1 | 2/2008 | Okabe et al. |
| 2008/0091153 A1 | 4/2008 | Harvie |
| 2008/0091158 A1 | 4/2008 | Yang |
| 2008/0234642 A1 | 9/2008 | Patterson et al. |
| 2008/0281282 A1 | 11/2008 | Finger et al. |
| 2008/0287894 A1 | 11/2008 | Van Den Heuvel et al. |
| 2009/0025717 A1 | 1/2009 | Pinel |
| 2009/0056003 A1 | 3/2009 | Ivie et al. |
| 2009/0192482 A1 | 7/2009 | Dodge, II et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0121289 A1 | 5/2010 | Parks et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028922 A1 | 2/2011 | Kay et al. |
| 2011/0034889 A1 | 2/2011 | Smith |
| 2011/0040267 A1 | 2/2011 | Wada et al. |
| 2011/0040271 A1 | 2/2011 | Rogers et al. |
| 2011/0054426 A1 | 3/2011 | Stewart et al. |

(56) References Cited

U.S. PATENT DOCUMENTS

| | | |
|---|---|---|
| 2011/0060300 A1 | 3/2011 | Weig et al. |
| 2011/0077495 A1 | 3/2011 | Gilbert |
| 2011/0172620 A1 | 7/2011 | Khambatta |
| 2011/0172625 A1 | 7/2011 | Wada et al. |
| 2011/0202024 A1 | 8/2011 | Cozzens |
| 2012/0035577 A1 | 2/2012 | Tomes et al. |
| 2012/0103347 A1 | 5/2012 | Wheaton et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0330256 A1 | 12/2012 | Wilcox et al. |
| 2013/0006206 A1 | 1/2013 | Wada et al. |
| 2013/0053804 A1 | 2/2013 | Soerensen et al. |
| 2013/0096523 A1 | 4/2013 | Chang et al. |
| 2014/0031774 A1 | 1/2014 | Bengtson |
| 2014/0157499 A1 | 6/2014 | Suzuki et al. |
| 2014/0182051 A1 | 7/2014 | Tanimoto et al. |
| 2014/0196189 A1 | 7/2014 | Lee et al. |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0047114 A1 | 2/2015 | Ramirez |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0359660 A1 | 12/2015 | Harvie |
| 2015/0366699 A1 | 12/2015 | Nelson |
| 2016/0029998 A1 | 2/2016 | Brister et al. |
| 2016/0038356 A1 | 2/2016 | Yao et al. |
| 2016/0058322 A1 | 3/2016 | Brister et al. |
| 2016/0100976 A1 | 4/2016 | Conway et al. |
| 2016/0106604 A1 | 4/2016 | Timm |
| 2016/0278662 A1 | 9/2016 | Brister et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0143534 A1 | 5/2017 | Sanchez |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252202 A9 | 9/2017 | Sanchez et al. |
| 2017/0266031 A1 | 9/2017 | Sanchez et al. |
| 2017/0312116 A1 | 11/2017 | Laniado |
| 2017/0333244 A1 | 11/2017 | Laniado |
| 2017/0042748 A1 | 12/2017 | Griffin |
| 2017/0348139 A1 | 12/2017 | Newton et al. |
| 2018/0008451 A1 | 1/2018 | Stroebech |
| 2018/0008804 A1 | 1/2018 | Laniado |
| 2018/0028349 A1 | 2/2018 | Newton et al. |
| 2018/0049910 A1 | 2/2018 | Newton |
| 2018/0064572 A1 | 3/2018 | Wiltshire |
| 2018/0200101 A1 | 7/2018 | Su |
| 2018/0228642 A1 | 8/2018 | Davis et al. |
| 2019/0038451 A1 | 2/2019 | Harvie |
| 2019/0142624 A1 | 5/2019 | Sanchez et al. |
| 2019/0224036 A1 | 7/2019 | Sanchez et al. |
| 2019/0314190 A1 | 10/2019 | Sanchez et al. |
| 2020/0046544 A1 | 2/2020 | Godinez et al. |
| 2020/0085610 A1 | 3/2020 | Cohn et al. |
| 2021/0069008 A1 | 3/2021 | Blabas et al. |

FOREIGN PATENT DOCUMENTS

| | | |
|---|---|---|
| CN | 1602825 A | 4/2005 |
| CN | 1720888 A | 1/2006 |
| CN | 101262836 A | 9/2008 |
| CN | 1 0371 71 80 A | 4/2014 |
| CN | 107847384 A | 3/2018 |
| DE | 9407554.9 U1 | 5/1995 |
| DE | 4443710 A1 | 6/1995 |
| DE | 102011103783 A1 | 12/2012 |
| DK | 9600118 | 11/1996 |
| EP | 0032138 A2 | 7/1981 |
| EP | 0066070 B1 | 12/1982 |
| EP | 0119143 B1 | 11/1988 |
| EP | 0610638 A1 | 8/1994 |
| EP | 0613355 A1 | 9/1994 |
| EP | 0613355 B1 | 1/1997 |
| EP | 1382318 A1 | 1/2004 |
| EP | 1382318 B1 | 5/2006 |
| EP | 2180907 A1 | 5/2010 |
| EP | 2380532 A1 | 10/2011 |
| EP | 2879534 B1 | 3/2017 |
| EP | 3169292 B1 | 11/2019 |
| GB | 1467144 A | 3/1977 |
| GB | 2106395 A | 4/1983 |
| GB | 2148126 B | 7/1987 |
| GB | 2191095 A | 12/1987 |
| GB | 2199750 A | 7/1988 |
| GB | 2260907 A | 5/1993 |
| GB | 2469496 A | 10/2010 |
| JP | S5410596 A | 1/1979 |
| JP | S5410596 Y2 | 5/1979 |
| JP | H0267530 A | 3/1990 |
| JP | H02103871 A | 4/1990 |
| JP | H0460220 A | 2/1992 |
| JP | H05123349 A | 5/1993 |
| JP | H11113946 A | 4/1999 |
| JP | H11290365 A | 10/1999 |
| JP | 2000185068 A | 7/2000 |
| JP | 3087938 B2 | 9/2000 |
| JP | 2001054531 | 2/2001 |
| JP | 2001054531 A | 2/2001 |
| JP | 2001276107 A | 10/2001 |
| JP | 2001276108 A | 10/2001 |
| JP | 2004267530 A | 9/2004 |
| JP | 2005066325 A | 3/2005 |
| JP | 2006026108 A | 2/2006 |
| JP | 3123547 B2 | 6/2006 |
| JP | 2006204868 A | 8/2006 |
| JP | 3132659 B2 | 5/2007 |
| JP | 4039641 B2 | 11/2007 |
| JP | 4747166 B2 | 5/2011 |
| JP | 2011224070 A | 11/2011 |
| JP | 2012523869 A | 10/2012 |
| JP | 2015092945 A | 5/2015 |
| JP | 3198994 B2 | 7/2015 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9309736 A2 | 5/1993 |
| WO | 9309736 A3 | 6/1993 |
| WO | 9600096 A1 | 1/1996 |
| WO | 9830336 A1 | 7/1998 |
| WO | 0057784 A1 | 10/2000 |
| WO | 0145618 A1 | 6/2001 |
| WO | 0145621 A1 | 6/2001 |
| WO | 03071931 A2 | 9/2003 |
| WO | 03071931 A3 | 2/2004 |
| WO | 2004019836 A1 | 3/2004 |
| WO | 2005089687 A2 | 9/2005 |
| WO | 2005107661 A2 | 11/2005 |
| WO | 2007007845 A1 | 1/2007 |
| WO | 2007042823 A2 | 4/2007 |
| WO | 2007128156 A3 | 2/2008 |
| WO | 2008078117 A1 | 7/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009007702 A4 | 7/2009 |
| WO | 2009101738 A1 | 8/2009 |
| WO | 2010030122 A3 | 7/2010 |
| WO | 2011018132 A1 | 2/2011 |
| WO | 2011018133 A1 | 2/2011 |
| WO | 2011024864 A1 | 3/2011 |

(56) References Cited

FOREIGN PATENT DOCUMENTS

| | | |
|---|---|---|
| WO | 2011054118 A1 | 5/2011 |
| WO | 2011107972 A1 | 9/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2013103291 A2 | 7/2013 |
| WO | 2013131109 A1 | 9/2013 |
| WO | 2014041534 A1 | 3/2014 |
| WO | 2015023599 A1 | 2/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016200088 A1 | 12/2016 |
| WO | 2017205446 A1 | 11/2017 |
| WO | 2017209779 A1 | 12/2017 |
| WO | 2017210524 A1 | 12/2017 |
| WO | 2018022414 A1 | 2/2018 |
| WO | 2018056953 A1 | 3/2018 |
| WO | 2018138513 A1 | 8/2018 |
| WO | 2018152156 A1 | 8/2018 |
| WO | 2018235065 A1 | 12/2018 |
| WO | 2020038822 A1 | 2/2020 |
| WO | 2020120657 A1 | 6/2020 |
| WO | 2021094352 A1 | 5/2021 |

OTHER PUBLICATIONS

Office Action for U.S. Appl. No. 14/947,759, dated Mar. 17, 2006.
AMXDmax In-Flight Bladder Relief; Omni Medical 2015; Omni Medical Systems, Inc.
Final Office Action for U.S. Appl. No. 14/947,759, dated Apr. 8, 2016.
International Search Report and Written Opinion for International Patent Application No. PCT/US16/49274, dated Dec. 1, 2016 (11 pages).
International Search Report and Written Opinion of the International Searching Authority for International Patent Application No. PCT/US2017/035625, dated Aug. 15, 2017 (17 pages).
Non-Final Office Action for U.S. Appl. No. 14/947,759, dated Mar. 17, 2016.
U.S. Appl. No. 15/171,968, filed Jun. 2, 2016.
Parmar, "10 Finalists Chosen for Dare-to-Dream Medtech Design Challenge (PUreWick)," Design Services, Nov. 10, 2014 (3 pages).
Purewick, "Incontinence Relief for Women" Presentation, (7 pages), Sep. 23, 2015.
Pytlik, "Super Absorbent Polymers," University of Buffalo http://www.courses.sens.buffalo.edu/ce435/Diapers/Diapers.html, accessed on Feb. 17, 2017.
Non-Final Office Action for U.S. Appl. No. 15/171,968 dated Jun. 12, 2018.
Non-Final Office Action for U.S. Appl. No. 15/611,587 dated Dec. 29, 2017.
Corrected International Search Report and Written Opinion for International Application No, PCT/US2017/043025 dated Jan. 11, 2018.
International Search Report and Written Opinion for International Application No. PCT/US2017/043025 dated Oct. 18, 2017.
International Search Report and Written Opinion for International Application No. PCT/US2018/015968 dated Apr. 6, 2018.
Non-Final Office Action for U.S. Appl. No. 15/221,106 dated Jun. 5, 2018.
Non-Final Office Action for U.S. Appl. No. 15/238,427 dated Aug. 8, 2018.
Non-Final Office Action for U.S. Appl. No. 15/260,103 dated Sep. 26, 2018.
Non-Final Office Action for U.S. Appl. No. 15/611,587 dated Jul. 13, 2018.
U.S. Appl. No. 15/612,325, filed Jun. 2, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
"Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
"Step by Step How Ur24 WorksHome", http://medicalpatentur24.com, last accessed Dec. 6, 2017, Aug 30, 2017, 4 pages.
Advisory Action for U.S. Appl. No. 15/238,427 dated Apr. 10, 2019.
Corrected Notice of Allowability for U.S. Appl. No. 15/221,106 dated Jul. 2, 2019.
Final Office Action for U.S. Appl. No. 15/171,968 dated Mar. 19, 2019.
Final Office Action for U.S. Appl. No. 15/221,106 dated Jan. 23, 2019.
Final Office Action for U.S. Appl. No. 15/238,427 dated Jan. 2, 2019.
Final Office Action for U.S. Appl. No. 15/260,103 dated Feb. 14, 2019.
Issue Notification for U.S. Appl. No. 15/611,587 dated Feb. 20, 2019.
Notice of Allowance for U.S. Appl. No. 15/221,106 dated May 1, 2019.
Notice of Allowance for U.S. Appl. No. 15/238,427 dated May 23, 2019.
Notice of Allowance for U.S. Appl. No. 15/260,103 dated Jun. 7, 2019.
Notice of Allowance for U.S. Appl. No. 15/611,587 dated Dec. 21, 2018.
U.S. Appl. No. 15/221,106, filed Jul. 27, 2016.
U.S. Appl. No. 16/369,676, filed Mar. 29, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
International Search Report and Written Opinion from International Application No. PCT/US2019/029608 dated Sep. 3, 2019.
International Search Report and Written Opinion from International Application No. PCT/US2019/029609 dated Sep. 3, 2019.
International Search Report and Written Opinion from International Application No. PCT/US2019/029610 dated Sep. 3, 2019.
International Search Report and Written Opinion from International Application No. PCT/US2019/029611 dated Jul. 3, 2019.
International Search Report and Written Opinion from International Application No. PCT/US2019/029613 dated Jul. 3, 2019.
International Search Report and Written Opinion from International Application No. PCT/US2019/029614 dated Sep. 26, 2019.
International Search Report and Written Opinion from International Application No. PCT/US2019/029616 dated Aug. 30, 2019.
Issue Notification for U.S. Appl. No. 15/221,106 dated Jul. 24, 2019.
Issue Notification for U.S. Appl. No. 15/238,427 dated Jul. 24, 2019.
Issue Notification for U.S. Appl. No. 15/260,103 dated Aug. 7, 2019.
Non-Final Office Action for U.S. Appl. No. 15/171,968 dated Aug. 20, 2019.
Defendant and Counterclaim Plaintiff Sage Products, LLC's Answer, Defenses, and Counterclaims to Plaintiff's Amended Complaint, Nov. 1, 2019.
Non-Final Office Action for U.S. Appl. No. 15/171,968 dated May 11, 2020.
Non-Final Office Action for U.S. Appl. No. 29/694,002 dated Jun. 24, 2020.
Notice of Allowance for U.S. Appl. No. 29/624,661 dated Jul. 10, 2020.

(56) References Cited

OTHER PUBLICATIONS

Notice of Allowance for U.S. Appl. No. 29/624,661 dated May 14, 2020.
U.S. Appl. No. 16/904,868, filed Jun. 18, 2020.
U.S. Appl. No. 16/905,400, filed Jun. 18, 2020.
PureWick's Response to Interrogatory No. 9 in *PureWick, LLC v. Sage Products, LLC*, Case No. 19-1508-MN, 2020, 6 pages.
"Underwear that absorbs your period", Thinx!, https://www.shethinx.com/pages/thinx-it-works last accessed Jun. 24, 2020, 7 pages.
Hollister, "Retracted Penis Pouch by Hollister", Vitality Medical.com, https://www.vitalitymedical.com/hollister-retracted-penis-pouch.html last accessed Jun. 24, 2020, 6 pages.
Newman, "Curriculum Vitae", Petition for Interparties Review, 2020, pp. 1-199.
Newman, et al., "The Urinary Incontinence Sourcebook", Petition for Interparties Review, 1997, 23 pages.
Advisory Action for U.S. Appl. No. 14/722,613 dated Mar. 4, 2019.
Final Office Action for U.S. Appl. No. 14/722,613 dated Nov. 29, 2018.
Final Office Action for U.S. Appl. No. 15/171,968 dated Feb. 14, 2020.
Final Office Action for U.S. Appl. No. 29/624,661 dated Feb. 18, 2020.
Non-Final Office Action for U.S. Appl. No. 14/722,613 dated Jun. 13, 2019.
Non-Final Office Action for U.S. Appl. No. 15/612,325 dated Mar. 19, 2020.
U.S. Appl. No. 15/260,103, filed Sep. 8, 2016.
U.S. Appl. No. 15/611,587, filed Jun. 1, 2017.
U.S. Appl. No. 16/433,773, filed Jun. 6, 2019.
U.S. Appl. No. 16/478,180, filed Jul. 16, 2019.
U.S. Appl. No. 62/452,437, filed Jan. 31, 2017.
U.S. Appl. No. 62/994,912, filed Mar. 26, 2020.
Final Office Action for U.S. Appl. No. 15/612,325 dated Sep. 17, 2020.
Non-Final Office Action for U.S. Appl. No. 16/899,956 dated Oct. 16, 2020.
Non-Final Office Action for U.S. Appl. No. 16/904,868 dated Nov. 25, 2020.
Non-Final Office Action for U.S. Appl. No. 16/905,400 dated Dec. 2, 2020.
Non-Final Office Action for U.S. Appl. No. 17/088,272 dated Jan. 25, 2021.
Notice of Allowance for U.S. Appl. No. 15/171,968 dated Nov. 6, 2020.
Notice of Allowance for U.S. Appl. No. 15/612,325 dated Jan. 21, 2021.
Notice of Allowance for U.S. Appl. No. 29/624,661 dated Sep. 29, 2020.
Notice of Allowance for U.S. Appl. No. 29/694,002 dated Oct. 16, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 63/134,287, filed Jan. 6, 2021.
U.S. Appl. No. 63/134,632, filed Jan. 7, 2021.
Sage's Initial Invalidity Contentions Regarding U.S. Pat. No. 8,287,508; U.S. Pat. No. 10,226,375; and U.S. Pat. No. 10,390,989, May 29, 2020, 193 pages.
Sage's Supplemental and Initial Invalidity Contentions Regarding U.S. Pat. No. 8,287,508; U.S. Pat. No. 10,226,375; U.S. Pat. No. 10,390,989 and Initial Invalidity Contentions Regarding U.S. Pat. No. 10,376,407, Aug. 21, 2020, 277 pages.
Sage's Second Supplemental Invalidity Contentions Regarding U.S. Pat. No. 8,287,508, U.S. Pat. No. 10,226,375, U.S. Pat. No. 10,390,989, and U.S. Pat. No. 10,376,407, 292 pages.
Excerpts from the 508 (U.S. Pat. No. 8,278,508) Patent's Prosecution History, 2020, 99 pages.
Plaintiff's Opening Claim Construction Brief, Case No. 19-1508-MN, Oct. 16, 2020, 26 pages.
Plaintiff's Identification of Claim Terms and Proposed Constructions, Case No. 19-1508-MN, 3 pages.
Sage's Preliminary Identification of Claim Elements and Proposed Constructions for U.S. Pat. No. 8,287,508, U.S. Pat. No. 10,226,376, U.S. Pat. No. 10,390,989 and U.S. Pat. No. 10,376,407, Case No. 19-1508-MN, 7 pages.
Corrected Certificate of Service, Case No. IPR2020-01426, U.S. Pat. No. 8,287,508, 2020, 2 pages.
"3 Devices Take Top Honors in Dare-To-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, Omni Medical, 8 pages.
"AMXDX—Advanced Mission Extender Device Brochure", Omni Medical, Omni Brochure—http://www.omnimedicalsys.com/uploads/AMXDFixedWing.pdf, 2 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"In Flight Bladder Relief", Omni Medical, Omni Presentation https://www.omnimedicalsys.com/uploads/AMXDmax_HSD.pdf, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Hollister, Female Urinary and Pouch and Male Urinary Pouch Brochure, 2011, 1 page.
MacAulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newton, et al., "Measuring Safety, Effectiveness and Ease of Use of PureWick in the Management of Urinary Incontinence in Bedbound Women: Case Studies", Jan. 8, 2016, 11 pages.
Sachtman, "New Relief for Pilots? It Depends", Wired, https://www.wired.com/2008/05/pilot-relief/, 2008, 2 pages.
Advisory Action for U.S. Appl. No. 16/905,400 dated Jun. 9, 2021.
Corrected Notice of Allowability for U.S. Appl. No. 15/612,325 dated Mar. 17, 2021.
Final Office Action for U.S. Appl. No. 16/899,956 dated Apr. 19, 2021.
Final Office Action for U.S. Appl. No. 16/904,868 dated Mar. 26, 2021.
Final Office Action for U.S. Appl. No. 16/905,400 dated Apr. 6, 2021.
Final Office Action for U.S. Appl. No. 17/088,272 dated May 25, 2021.
Issue Notification for U.S. Appl. No. 15/171,968 dated Mar. 3, 2021.
Issue Notification for U.S. Appl. No. 15/612,325 dated Mar. 24, 2021.
Notice of Allowance for U.S. Appl. No. 15/171,968 dated Feb. 16, 2021.

(56) References Cited

OTHER PUBLICATIONS

Notice of Allowance for U.S. Appl. No. 15/612,325 dated Feb. 19, 2021.
Notice of Allowance for U.S. Appl. No. 29/624,661 dated Apr. 28, 2021.
Notice of Allowance for U.S. Appl. No. 29/694,002 dated Apr. 29, 2021.
Notice of Allowance for U.S. Appl. No. 29/694,002 dated Jan. 29, 2021.
Notice to File Missing Parts for U.S. Appl. No. 17/179,116 dated Mar. 3, 2021.
Restriction Requirement for U.S. Appl. No. 16/478,180 dated May 25, 2021.
U.S. Appl. No. 17/179,116, filed Feb. 18, 2021.
U.S. Appl. No. 17/330,657 dated May 26, 2021.
U.S. Appl. No. 63/148,723, filed Feb. 12, 2021.
Memorandum Order, Feb. 2021, 14 pgs.
BOEHRINGER CareDry System—Second Generation for Non-Invasive Urinary Management for Females, Mar. 2021, 3 pgs.
Decision Granting Institution of Inter Partes Review for patent No. 8,287,508, Case No. 2020-01426, Feb. 17, 2021, 39 pages.

\* cited by examiner

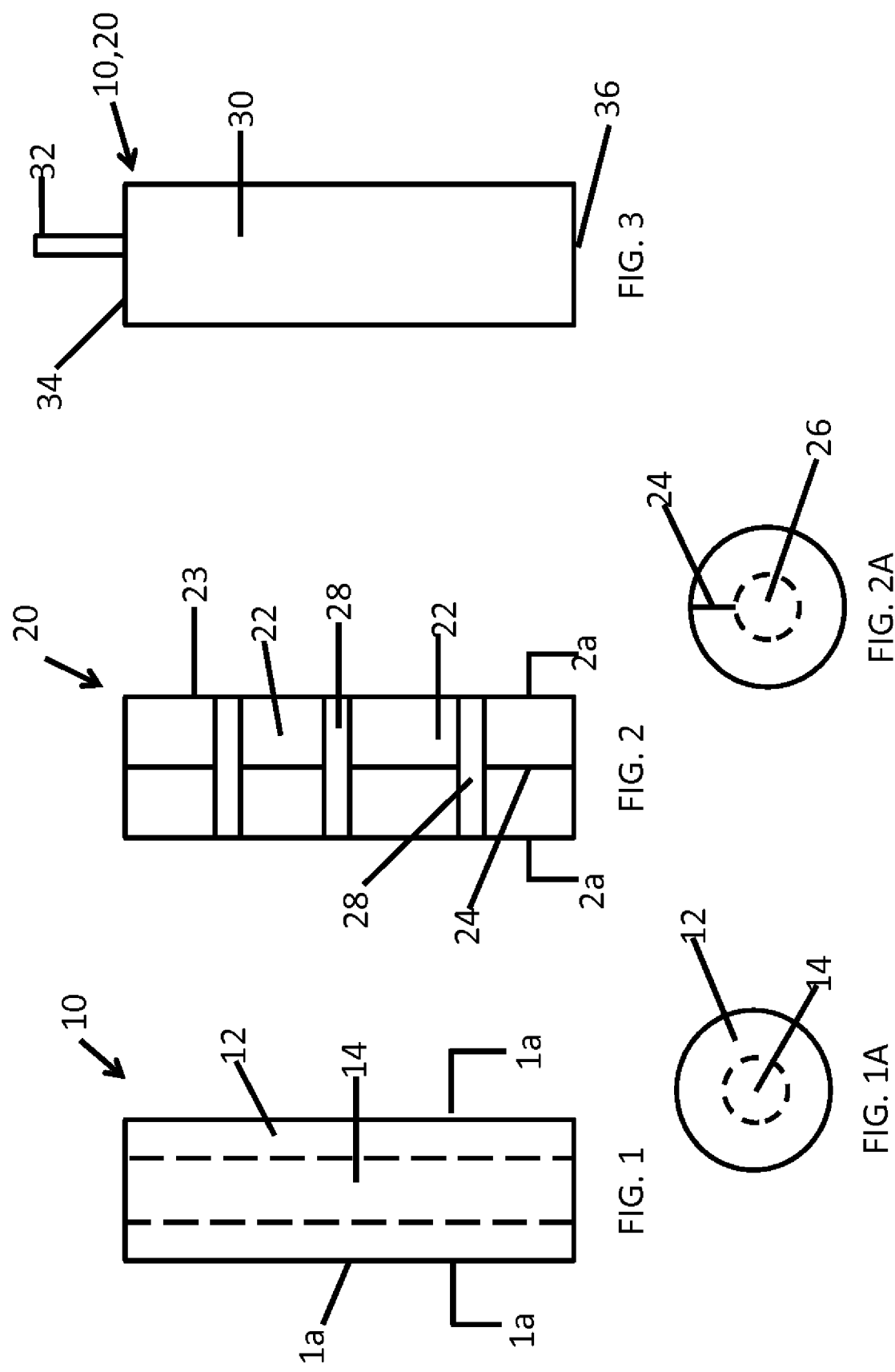

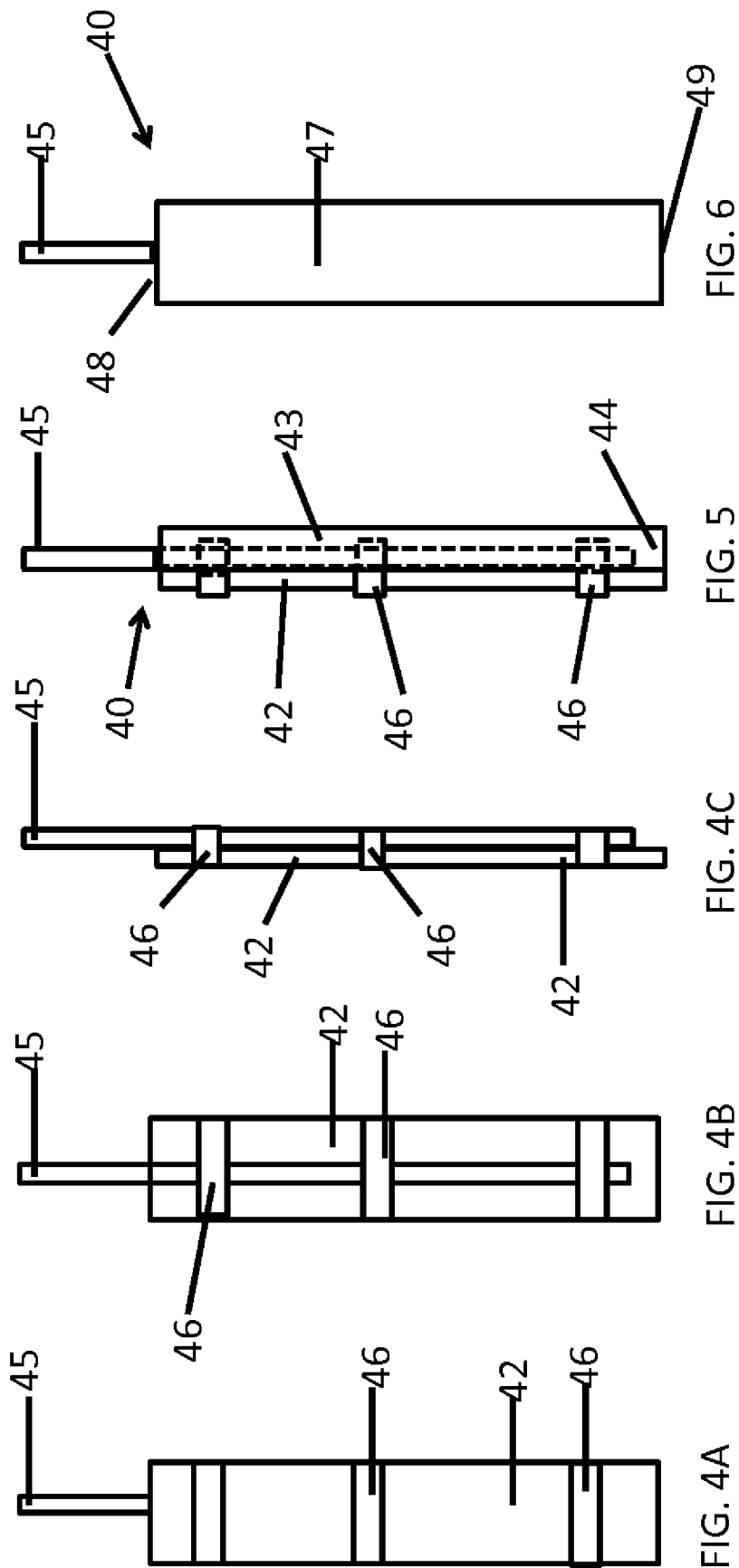

CONTAINER FOR COLLECTING LIQUID FOR TRANSPORT

CROSS-REFERENCE TO RELATED APPLICATIONS

This application claims the benefit of U.S. Provisional Patent Application No. 62/084,078 filed Nov. 25, 2014, the disclosure of which is herein incorporated by reference.

BACKGROUND OF THE INVENTION

The invention generally pertains to a container for collecting liquid for transport and is particularly directed to a container that can be used to so collect a liquid, such as urine, from the body of a person or an animal that the liquid can be readily transported from the container as the liquid is being collected.

A container for collecting urine and transporting the collected urine voided from a person's body is described in U.S. Pat. No. 8,287,508 to Robert A. Sanchez. The container described in said patent is made of plastic or some other material and defines a chamber for collecting urine. The container is closed, except for having an array of openings through which urine can be drawn into the chamber for collection and at least one outlet port through which urine can be drawn away from the chamber by a transport tube inserted into the chamber. The exterior of the container is configured for enabling a moisture-wicking article to be secured over the array of openings and for enabling the secured moisture-wicking article to be disposed in contact with the region of a female body surrounding the urethral opening. A vacuum pump is attached to the transport tube in order to create a partial vacuum in the chamber in order to draw urine into the chamber for collection of the urine and in order to draw the collected urine away from the chamber.

SUMMARY OF THE INVENTION

The invention provides a container for collecting liquid for transport, comprising: a web of flexible porous material defining at least a portion of a chamber in which liquid can be collected for transport; wherein the chamber is configured to receive a tube in a position within the chamber that enables said tube to transport liquid from the chamber while said liquid collects within the chamber upon being drawn through the web when a partial vacuum is applied within the chamber via said tube; wherein the porous material comprises a web of spun plastic fibers.

In one exemplary embodiment, the web of spun plastic fibers is configured to define an elongated portion of said chamber.

In another exemplary embodiment, a backing of non-permeable material covers a portion of the web and is so combined with the web as to further define the chamber.

The present invention is particularly useful for persons or animals during various circumstances. These circumstances include a condition such as incontinence or a disability that limits or impairs mobility. These circumstances also include restricted travel conditions, such as sometimes experienced by pilots, drivers, workers in hazardous areas, etc. These circumstances further include collection of urine for monitoring purposes or clinical testing.

Additional features of the present invention are described with reference to the detailed description.

BRIEF DESCRIPTION OF THE DRAWING

FIG. 1 is a plan view of one exemplary embodiment of a container according to the invention, with an interior chamber being shown by dashed lines.

FIG. 1A is a sectional view of the container shown in FIG. 1, taken along line 1a-1a in FIG. 1.

FIG. 2 is a plan view of a variation of the one exemplary embodiment of a container according to the invention.

FIG. 2A is a sectional view of the container shown in FIG. 2, taken along line 2a-2a in FIG. 2.

FIG. 3 is a plan view of the one exemplary embodiment of a container according to the invention, as shown in FIGS. 2 and 3, with a moisture wicking material being wrapped around the container and a liquid transport tube inserted within the chamber of the container.

FIGS. 4A, 4B and 4C are respectively front, rear and side views of a first portion of another exemplary embodiment of a container according to the invention in combination with a liquid transport tube.

FIG. 5 illustrates the portion of the container shown in FIG. 4C in combination with a backing to further define a chamber within the container.

FIG. 6 illustrates the other exemplary embodiment, with a moisture wicking material being wrapped around the container shown in FIG. 5 and a liquid transport tube inserted within the chamber of the container.

DETAILED DESCRIPTION

Referring to FIGS. 1 and 1A, one exemplary embodiment of a container 10 according to the present invention includes a web 12 of flexible porous material defining at least a portion of a chamber 14 in which liquid can be collected for transport. The web 12 of spun plastic fibers is configured to define an elongated portion of the chamber. Preferably, the container 10 is formed to have a tubular shape. The exterior shape of the container may be cylindrical or non-cylindrical.

The chamber 14 is configured to receive a tube in a position within the chamber 14 that enables the tube to transport from the chamber 14 liquid that is collected within the chamber 14 upon the liquid being drawn through the web 12.

FIGS. 2 and 2A show a variation of the one exemplary embodiment that is shown in FIGS. 1 and 1A. In this variation, a container 20 includes web 22 of spun plastic formed in a flexible sheet 23. The web 22 is then formed to have a tubular shape by flexing the sheet 23 so that opposite sides of the sheet 23 are held closely together, or meet as shown at 24, to define an elongated chamber 26. The opposite sides of the sheet 23 are held together by adhesive bands 28, or by other means, such as glue, or by compression created by a moisture-wicking article wrapped around the perimeter.

The container 20 is configured and sized to receive a moisture-wicking article over the flexed sheet 23 and to be able to dispose the received moisture-wicking article 20 in contact with a region of the body surrounding the urethral opening.

Referring further to FIG. 3, a moisture wicking material 30 is wrapped around the container 10, 20 and a liquid transport tube 32 is inserted within the chamber 14, 26 of the container 10, 20. In an alternative version related to the variation shown in FIGS. 2 and 2A, the moisture wicking material 30 is attached to or sprayed onto one side of the web 22 prior to the sheet 23 being flexed in order to define the elongated chamber 26.

The transport tube 32 is inserted through an outlet port at one end 34 of the container 10, 20 to a position within the chamber 14, 26 that enables the tube 32 to transport liquid collected within the chamber 14, 26 upon the liquid passing through the web 12, 22.

The other end 36 of the container 10, 20 is closed. The transport tube 32 is coupled to a vacuum pump, which can be used to create a partial vacuum in the chamber 14, 26 of the container 10, 20 to enable the tube 32 to transport liquid from the chamber 14, 26 while the liquid collects within the chamber 14, 26 upon being drawn through the web 12, 22 when the partial vacuum is applied within the chamber 14, 26 via the tube 32.

Referring to FIGS. 4A, 4B, 4C and 5, another exemplary embodiment of a container 40 according to the present invention includes a porous flexible web 42 of spun plastic fibers and a backing 43 (as shown in FIG. 5) of non-permeable material covering a portion of the web 42.

The transport tube 45 is secured to the web 42, as shown in FIG. 4C. In this embodiment, an adhesive tape 46 is used to secure the transport tube 45 to the web 42. In other embodiments, the transport tube 45 is secured by other means.

The backing 43 is so combined with the web 42 as to define a portion of a chamber 44 in which liquid can be collected for transport, as shown in FIG. 5. The chamber 44 is configured to receive a transport tube 45 in a position within the chamber 44 that enables the tube 45 to transport liquid collected within the chamber 44.

The transport tube 45 is secured to the web 42, as shown in FIG. 4C. In this embodiment, an adhesive tape 46 is used to secure the transport tube 45 to the web 42. In other embodiments, the transport tube 45 is secured by other means.

Referring further to FIG. 6, the container 40 is configured and sized to receive a moisture-wicking article 47 over the web 42 and to be able to dispose the received moisture-wicking article 47 in contact with a region of the body surrounding the urethral opening.

The moisture-wicking material 47 is wrapped around the container 40, which has the liquid transport tube extending from the chamber 44 of the container. The transport tube 45 extends through an outlet port at one end 48 of the container 40 to a position within the chamber 44 that enables the tube 45 to transport liquid collected within the chamber 44. The other end 49 of the container 40 is closed. The transport tube 45 is coupled to a vacuum pump, which can be used to create a partial vacuum in the chamber 44 of the container 40 to enable the tube 45 to transport liquid from the chamber 44 while the liquid collects within the chamber 44 upon being drawn through the web 42 when the partial vacuum is applied within the chamber 44 via the tube 45.

Preferably, the spun plastic fibers include, and may consist of, spun polyester fibers, such as contained in a scouring pad. Polyester fibers are preferred because of their characteristic of not retaining undesirable odors. In alternative embodiments, the web is made of some other type of fibers.

For a female, the secured moisture-wicking article 20 is placed between the legs or labia and held snugly against the external urethra by pressure or friction from the user's body, by the pressure of the legs or by such means as an undergarment, elastic strips and/or adhesive tape. For a male, the secured moisture-wicking article is secured around the penis.

Different embodiments of a container for a urine collection device according to the invention are configured for use by both females and males, for both adult and pediatric applications, and for veterinary applications involving animals of different species and sizes.

The benefits specifically stated herein do not necessarily apply to every conceivable embodiment of the present invention. Further, such stated benefits of the present invention are only examples and should not be construed as the only benefits of the present invention.

While the above description contains many specificities, these specificities are not to be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. A container for collecting liquid for transport, the container comprising:
    a moisture-wicking material positioned to be disposed in contact with a body;
    a web of flexible porous material positioned directly adjacent to at least a portion of the moisture-wicking material and at least partially defining at least one wall;
    a closed end;
    a non-permeable material covering at least a portion of the web of flexible porous material; and
    a chamber having a first portion and a second portion, the first portion configured to receive at least a portion of a tube in a position within the chamber that enables said tube to transport liquid from the second portion of the chamber while said liquid collects within the second portion of the chamber upon being drawn through the web of flexible porous material when a partial vacuum is applied within the chamber via said tube, the first portion of the chamber including an interior surface at least partially defined by the at least one wall of the web of flexible porous material, and the second portion of the chamber positioned at the closed end and defined at least partially by a portion of the non-permeable material that is spaced from both the web of flexible porous material and an end of the tube when at least the portion of the tube is received in the first portion of the chamber;
    wherein the web of flexible porous material comprises a web of spun plastic fibers.

2. The container according to claim 1, wherein the web of spun plastic fibers defines an elongated portion of said chamber.

3. The container according to claim 2, wherein the web of spun plastic fibers is in a flexible sheet.

4. The container according to claim 1, wherein the non-permeable material covers a portion of the web of flexible porous material.

5. The container according to claim 1, wherein the web of spun plastic fibers includes spun polyester fibers.

6. The container according to claim 2, wherein the web of spun plastic fibers includes spun polyester fibers.

7. The container according to claim 4, wherein the web of spun plastic fibers includes spun polyester fibers.

8. The container according to claim 1, wherein the at least one wall of the web of flexible porous material extends about at least a portion of the chamber.

9. The container according to claim 1, wherein the moisture-wicking material is wrapped around at least a portion of a perimeter of the web of flexible porous material.

10. The container according to claim 1, wherein the chamber is configured to receive the tube through an open end of the container.

11. The container according to claim 1, wherein:
the moisture-wicking material is wrapped around at least a portion of a perimeter of the web of flexible porous material; and
the chamber is configured to receive the tube through an open end of the container.

12. The container according to claim 1, wherein the non-permeable material defines at least the first end of the chamber having the closed end.

13. The container according to claim 1, wherein the web of flexible porous material is absent from the second portion of the chamber at the closed end that is defined by the non-permeable material.

14. The container according to claim 1, wherein the second portion of the chamber at the closed end is defined at least partially on a first side by the non-permeable material and at least partially on a second side by the wall of the flexible porous material.

15. The container according to claim 13, wherein the second portion of the chamber at the closed end is adjacent to the portion of the non-permeable material defining the second portion of the chamber.

16. A container for collecting liquid for transport, the container comprising:
a moisture-wicking material positioned to be disposed in contact with a body;
a flexible porous material including spun plastic fibers positioned directly adjacent to at least a portion of the moisture-wicking material;
a non-permeable material, at least a portion of the non-permeable material covering a portion of the porous material;
a first end having an outlet port configured to receive a tube therethrough;
a closed second end distal to the first end; and
a chamber defined at least partially by a portion of the flexible porous material, at least a portion of the chamber being positioned at the closed second end and defined at least partially by a portion of the non-permeable material that is spaced from the flexible porous material.

17. The container according to claim 16, wherein the flexible porous material is absent from the portion of the chamber at the closed second end.

18. The container according to claim 16, wherein the portion of the chamber positioned at the closed second end is defined at least partially on a first side by the non-permeable material and at least partially on a second side by the flexible porous material.

* * * * *